(12) United States Patent
Portman

(10) Patent No.: US 8,008,479 B2
(45) Date of Patent: Aug. 30, 2011

(54) ORGANIC COMPOUNDS

(75) Inventor: Robert Portman, Pratteln (CH)

(73) Assignee: Novartis AG, Basel (CH)

( * ) Notice: Subject to any disclaimer, the term of this patent is extended or adjusted under 35 U.S.C. 154(b) by 319 days.

(21) Appl. No.: 12/296,969

(22) PCT Filed: Apr. 11, 2007

(86) PCT No.: PCT/EP2007/003213
§ 371 (c)(1),
(2), (4) Date: Oct. 13, 2008

(87) PCT Pub. No.: WO2007/118651
PCT Pub. Date: Oct. 25, 2007

(65) Prior Publication Data
US 2009/0137797 A1    May 28, 2009

(30) Foreign Application Priority Data

Apr. 13, 2006 (GB) .................. 0607532.9
May 23, 2006 (GB) .................. 0610244.6

(51) Int. Cl.
 C07D 209/20 (2006.01)
 C07D 403/12 (2006.01)
 C07D 223/10 (2006.01)

(52) U.S. Cl. .................................. 540/527
(58) Field of Classification Search ........... 540/527
See application file for complete search history.

(56) References Cited

FOREIGN PATENT DOCUMENTS

| WO | WO 96/026183 A1 | 8/1996 |
| WO | 98/07694 | 2/1998 |
| WO | WO 01/085696 A1 | 11/2001 |

*Primary Examiner* — Bruck Kifle
(74) *Attorney, Agent, or Firm* — John B. Alexander

(57) ABSTRACT

A process for preparing compounds of formula (I) or a solvate or hydrate thereof, where R, $R^1$, $R^2$, $R^3$ and $R^5$ have the meanings as indicated in the specification. Such compounds are useful in the treatment of a number of conditions associated with substance P and neurokinin.

5 Claims, No Drawings

ORGANIC COMPOUNDS

This invention relates to the preparation of organic compounds, particularly an acylaminoalkylene amide derivative substance P antagonist.

More specifically, the present invention relates to a process for preparing compounds of formula I

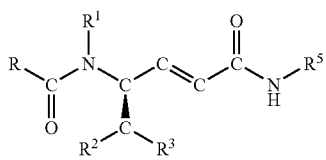
I or a solvate or hydrate thereof, where
R is phenyl that is unsubstituted or is substituted by 1, 2 or 3 substituents selected from the group consisting of halogen, $C_1$-$C_7$-alkyl, trifluoromethyl, hydroxy and $C_1$-$C_7$-alkoxy;
$R^1$ is hydrogen or $C_1$-$C_7$-alkyl;
$R^2$ is hydrogen, $C_1$-$C_7$-alkyl or phenyl that is unsubstituted or is substituted by 1, 2 or 3 substituents selected from the group consisting of halogen, $C_1$-$C_7$-alkyl, trifluoromethyl, hydroxy and $C_1$-$C_7$-alkoxy;
$R^3$ is phenyl that is unsubstituted or is substituted by 1, 2 or 3 substituents selected from the group consisting of halogen, $C_1$-$C_7$-alkyl, trifluoromethyl, hydroxy and $C_1$-$C_7$-alkoxy, or $R^3$ is naphthyl, 1H-indol-3-yl or 1-$C_1$-$C_7$-alkyl-indol-3-yl; and
$R^5$ is $C_3$-$C_8$-cycloalkyl, D-azacycloheptan-2-on-3-yl or L-azacycloheptan-2-on-3-yl.

Compounds of formula I are useful in the treatment of a number of conditions associated with substance P and neurokinin.

N-[(E)-(R)-1-(3,4-Dichloro-benzyl)-3-((R)-2-oxo-azepan-3-ylcarbamoyl)-allyl]-N-methyl-3,5-bis-trifluoromethyl-benzamide is a particularly preferred compound of formula I. It is also known as N-[(R,R)-(E)-1-(3,4-dichlorobenzyl)-3-(2-oxoazepan-3-yl)-carbamoyl]-allyl-N-methyl-3,5-bis(trifluoromethyl)-benzamide and (4R)-4-[N'-methyl-N'-(3,5-bistrifluoromethyl-benzoyl)-amino]-4-(3,4-dichlorobenzyl)-but-2-enoic acid N-[(R)-epsilon-caprolactam-3-yl]-amide and has the chemical structure of formula A

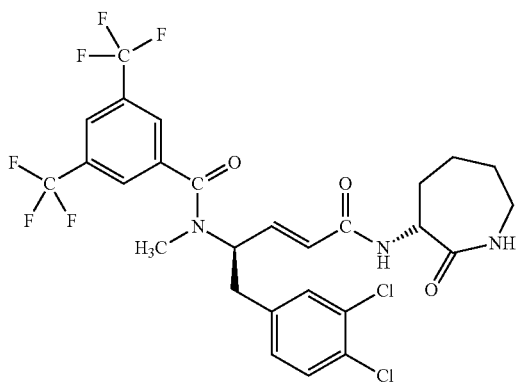
A

The compound of formula A, especially the hemihydrate thereof, is useful in the treatment of functional motility disorders of the viscera, such as irritable bowel syndrome or functional dyspepsia, especially diarrhoea-predominant irritable bowel syndrome.

Compounds of formula I can be prepared using the process described in international patent application WO 98/07694, the contents of which are incorporated herein by reference.

However the present invention relates to an improved process for preparing compounds of formula I and solvates and hydrates thereof, especially (4R)-4-[N'-methyl-N'-(3,5-bis-trifluoro-methyl-benzoyl)-amino]-4-(3,4-dichlorobenzyl)-but-2-enoic acid N-[(R)-epsilon-caprolactam-3-yl]-amide, with high levels of safety, hygiene and ease of handling. It also facilitates the achievement of good yields on a production scale.

In a first aspect, the present invention provides a process for preparing compounds of formula I

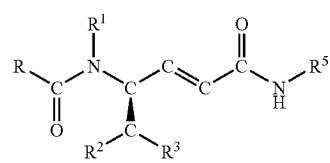
I or a solvate or hydrate thereof, where
R is phenyl that is unsubstituted or is substituted by 1, 2 or 3 substituents selected from the group consisting of halogen, $C_1$-$C_7$-alkyl, trifluoromethyl, hydroxy and $C_1$-$C_7$-alkoxy;
$R^1$ is hydrogen or $C_1$-$C_7$-alkyl;
$R^2$ is hydrogen, $C_1$-$C_7$-alkyl or phenyl that is unsubstituted or is substituted by 1, 2 or 3 substituents selected from the group consisting of halogen, $C_1$-$C_7$-alkyl, trifluoromethyl, hydroxy and $C_1$-$C_7$-alkoxy;
$R^3$ is phenyl that is unsubstituted or is substituted by 1, 2 or 3 substituents selected from the group consisting of halogen, $C_1$-$C_7$-alkyl, trifluoromethyl, hydroxy and $C_1$-$C_7$-alkoxy, or $R^3$ is naphthyl, 1H-indol-3-yl or 1-$C_1$-$C_7$-alkyl-indol-3-yl; and
$R^5$ is $C_3$-$C_8$-cycloalkyl, D-azacycloheptan-2-on-3-yl or L-azacycloheptan-2-on-3-yl,
the process comprising the steps of:
(a) reacting a compound of formula II

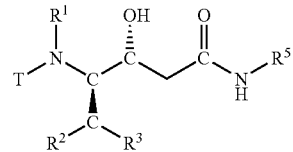
II where $R^1$, $R^2$, $R^3$ and $R^5$ are as hereinbefore defined and T is a protecting group, with a base to form a compound of formula III

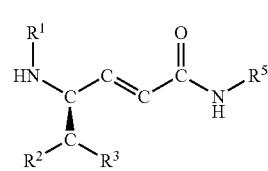
III where $R^1$, $R^2$, $R^3$ and $R^5$ are as hereinbefore defined; and (b) reacting a compound of formula III where $R^1$, $R^2$, $R^3$ and $R^5$ are as hereinbefore defined with a compound of formula IV

IV where R is phenyl that is unsubstituted or is substituted by 1, 2 or 3 substituents selected from the group consisting of halogen, $C_1$-$C_7$-alkyl, trifluoromethyl, hydroxy and $C_1$-$C_7$-alkoxy, and X is halo, in the presence of a base to form a compound of formula I, and (c) optionally, forming a desired solvate or hydrate thereof.

In a second aspect, the present invention provides a process for preparing compounds of formula I

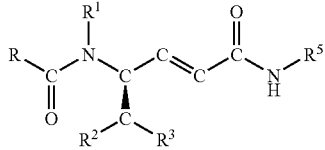
I or a solvate or hydrate thereof, where

R is phenyl that is unsubstituted or is substituted by 1, 2 or 3 substituents selected from the group consisting of halogen, $C_1$-$C_7$-alkyl, trifluoromethyl, hydroxy and $C_1$-$C_7$-alkoxy;

$R^1$ is hydrogen or $C_1$-$C_7$-alkyl;

$R^2$ is hydrogen, $C_1$-$C_7$-alkyl or phenyl that is unsubstituted or is substituted by 1, 2 or 3 substituents selected from the group consisting of halogen, $C_1$-$C_7$-alkyl, trifluoromethyl, hydroxy and $C_1$-$C_7$-alkoxy;

$R^3$ is phenyl that is unsubstituted or is substituted by 1, 2 or 3 substituents selected from the group consisting of halogen, $C_1$-$C_7$-alkyl, trifluoromethyl, hydroxy and $C_1$-$C_7$-alkoxy, or $R^3$ is naphthyl, 1H-indol-3-yl or 1-$C_1$-$C_7$-alkyl-indol-3-yl; and $R^5$ is $C_3$-$C_8$-cycloalkyl, D-azacycloheptan-2-on-3-yl or L-azacycloheptan-2-on-3-yl;

the process comprising the steps of:

(i) reacting a compound of formula V

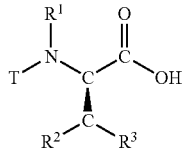
V where $R^1$, $R^2$ and $R^3$ are as hereinbefore defined and T is a protecting group with 2,2-dimethyl-[1,3]dioxane-4,6-dione in the presence of a base to form a compound of formula VI

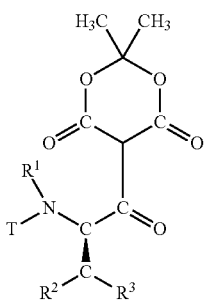
VI where $R^1$, $R^2$ and $R^3$ are as hereinbefore defined and T is a protecting group;

(ii) reacting the compound of formula VI where $R^1$, $R^2$ and $R^3$ are as hereinbefore defined and T is a protecting group with methanol to give a compound of formula VII

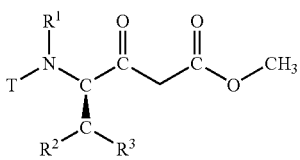
VII where $R^1$, $R^2$ and $R^3$ are as hereinbefore defined and T is a protecting group;

(iii) reducing the compound of formula VII where $R^1$, $R^2$ and $R^3$ are as hereinbefore defined and T is a protecting group to form a compound of formula VIII

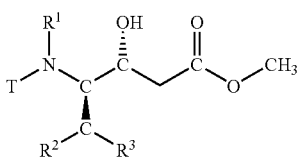
VIII where $R^1$, $R^2$ and $R^3$ are as hereinbefore defined and T is a protecting group;

(iv) hydrolysing the compound of formula VIII where $R^1$, $R^2$ and $R^3$ are as hereinbefore defined and T is a protecting group to give the corresponding carboxylic acid of formula IX

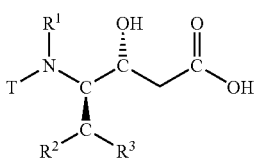
IX where $R^1$, $R^2$ and $R^3$ are as hereinbefore defined and T is a protecting group;

(v) reacting the compound of formula IX where $R^1$, $R^2$ and $R^3$ are as hereinbefore defined and T is a protecting group with a compound of formula X $$H_2N-R^5 \qquad X$$

where $R^5$ is $C_3$-$C_8$-cycloalkyl, D-azacycloheptan-2-on-3-yl or L-azacycloheptan-2-on-3-yl to form a compound of formula II

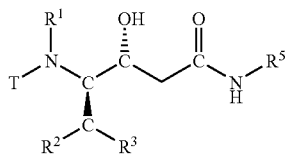

where $R^1$, $R^2$ and $R^3$ are as hereinbefore defined and T is a protecting group and $R^5$ is $C_3$-$C_8$-cycloalkyl, D-azacycloheptan-2-on-3-yl or L-azacycloheptan-2-on-3-yl;
(vi) optionally, purifying the compound of formula II where $R^1$, $R^2$, $R^3$ and $R^5$ are as hereinbefore defined and T is a protecting group;
(vii) reacting the compound of formula II where $R^1$, $R^2$, $R^3$ and $R^5$ are as hereinbefore defined and T is a protecting group, with a base to form a compound of formula III

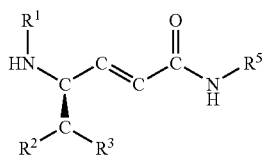

where $R^1$, $R^2$, $R^3$ and $R^5$ are as hereinbefore defined;
(viii) reacting the compound of formula III where $R^1$, $R^2$, $R^3$ and $R^5$ are as hereinbefore defined is reacted with a compound of formula IV

where R is phenyl that is unsubstituted or is substituted by 1, 2 or 3 substituents selected from the group consisting of halogen, $C_1$-$C_7$-alkyl, trifluoromethyl, hydroxy and $C_1$-$C_7$-alkoxy, and X is halo, in the presence of a base to form a compound of formula I where R, $R^1$, $R^2$, $R^3$ and $R^5$ are as hereinbefore defined; and
(ix) optionally, forming a desired solvate or hydrate thereof.

Terms used in the specification have the following meanings:

"Halogen" or "halo" as used herein denotes a element belonging to group 17 (formerly group VII) of the Periodic Table of Elements, which may be, for example, fluorine, chlorine, bromine or iodine. Preferably halogen or halo is chlorine or bromine, especially chlorine.

"$C_1$-$C_7$-alkyl" as used herein denotes a straight chain or branched alkyl group comprising 1 to 7 carbons, which may be, for example, methyl, ethyl, n-propyl, isopropyl, n-butyl, isobutyl, sec-butyl, tert-butyl, straight or branched pentyl, straight or branched hexyl or straight, or branched heptyl.

"$C_1$-$C_7$-alkoxy" as used herein denotes a straight chain or branched alkyl chain linked to O, which may be, for example, methoxy, ethoxy, n-propoxy, isopropoxy, n-butoxy, isobutoxy, sec-butoxy, tert-butoxy, straight or branched pentoxy, straight or branched hexyloxy, or straight or branched heptyloxy.

"$C_3$-$C_8$-cycloalkyl" as used herein denotes a fully saturated carbocyclic ring having 3 to 8 ring carbon atoms, for example a monocyclic group such as a cyclopropyl, cyclobutyl, cyclopentyl, cyclohexyl, cycloheptyl or cyclooctyl, or a bicyclic group such as bicycloheptyl or bicyclooctyl.

Throughout this specification and in the claims that follow, unless the context requires otherwise, the word "comprise", or variations such as "comprises" or "comprising", will be understood to imply the inclusion of a stated integer or step or group of integers or steps but not the exclusion of any other integer or step or group of integers or steps.

According to formula I, the following suitable, preferred, more preferred or most preferred aspects of the invention may be incorporated independently, collectively or in any combination.

R is suitably phenyl that is substituted by 1, 2 or 3 substituents selected from the group consisting of halogen, $C_1$-$C_7$-alkyl, trifluoromethyl, hydroxy and $C_1$-$C_7$-alkoxy. When R is phenyl substituted by $C_1$-$C_7$-alkyl it is suitably phenyl substituted by $C_1$-$C_4$-alkyl. However when R is phenyl substituted by $C_1$-$C_7$-alkoxy it is suitably phenyl substituted by $C_1$-$C_4$-alkoxy.

R is more suitably phenyl that is substituted at one or two positions, especially two positions, by trifluoromethyl. R is especially 3,5-bis-trifluoromethyl-phenyl.

$R^1$ is suitably $C_1$-$C_7$-alkyl, more suitably $C_1$-$C_4$-alkyl, but especially suitably methyl.

$R^1$ is suitably hydrogen or $C_1$-$C_7$-alkyl.

$R^2$ is suitably hydrogen.

$R^3$ is suitably phenyl that is substituted by 1, 2 or 3 substituents selected from the group consisting of halogen, $C_1$-$C_7$-alkyl, trifluoromethyl, hydroxy and $C_1$-$C_7$-alkoxy.

$R^3$ is more suitably phenyl that is substituted at one or two positions, especially two positions, by halo, especially chloro. $R^3$ is especially suitably 3,4-dichloro-phenyl.

$R^5$ is suitably D-azacycloheptan-2-on-3-yl.

Compounds of formula I or intermediate compounds that are used to prepare compounds of formula I can be pharmaceutically acceptable isotopically-labelled compounds of formula I or isotopically-labelled intermediate compounds that are used to prepare compounds of formula I respectively wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen e.g. $^2$H and $^3$H, carbon e.g. $^{11}$C, $^{13}$C and $^{14}$C, chlorine e.g. $^{36}$Cl, fluorine e.g. $^{18}$F, iodine e.g. $^{123}$I and $^{125}$I, nitrogen e.g. $^{13}$N and $^{15}$N, oxygen e.g. $^{15}$O, $^{17}$O and $^{18}$O, and sulfur e.g. $^{35}$S.

Certain isotopically-labelled compounds of formula I, for example those incorporating a radioactive isotope, are useful in drug and/or substrate tissue distribution studies. The radioactive isotopes tritium ($^3$H) and carbon-14 ($^{14}$C) are particularly useful for this purpose in view of their ease of incorporation and ready means of detection. Substitution with heavier isotopes such as deuterium ($^2$H) may afford certain therapeutic advantages that result from greater metabolic stability, for example increased in vivo half-life or reduced dosage requirements, and hence may be preferred in some circumstances. Substitution with positron emitting isotopes, such as $^{11}$C, $^{18}$F, $^{15}$O, and $^{13}$N can be useful in Positron Emission Topography (PET) studies for examining substrate receptor occupancy.

Isotopically-labelling compounds of formula I or isotopically-labelling compounds of intermediate compounds that are used to prepare compounds of formula I can generally be achieved by conventional techniques known to those skilled in the art or by processes analogous to those described in the accompanying examples using an appropriate isotopically-labelled reagent in place of the non-labelled reagent previously used.

Pharmaceutically acceptable solvates in accordance with the invention include those wherein the solvent of crystallisation may be isotopically substituted e.g. $D_2O$, $d_6$-acetone or $d_6$-DMSO.

Compounds of formula I can be prepared from a compound of formula V

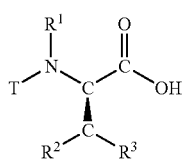

V where $R^1$, $R^2$ and $R^3$ are as hereinbefore defined and T is a protecting group by carrying out the following multi step process.

In process steps 1 and 2, a compound of formula V as defined above is elongated by two carbon atoms.

In the first of these steps a compound of formula V where $R^1$, $R^2$ and $R^3$ are as hereinbefore defined and T is a protecting group is reacted with 2,2-dimethyl-[1,3]dioxane-4,6-dione (meldrum's acid) in the presence of a base to form compounds of formula VI

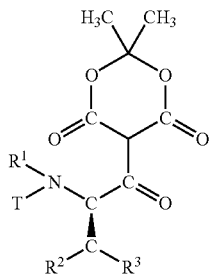

VI where $R^1$, $R^2$ and $R^3$ are as hereinbefore defined and T is a protecting group or analogously e.g. as hereinafter described in the Examples.

This step is suitably carried out in the presence of base, for example dimethyl-pyridin-4-yl-amine. It is conveniently carried out in an organic solvent, for example toluene. The reaction temperature may be, for example, from room temperature to 60° C., preferably from 25° C. to 35° C.

The protecting group T may be chosen from suitable protecting groups for the nature of the functional group, for example as described in Protective Groups in Organic Synthesis, T. W. Greene and P. G. M. Wuts, John Wiley & Sons Inc, Second Edition, 1991, which reference also describes procedures suitable for replacement of the protecting groups by hydrogen. The protecting group is suitably t-butoxycarbonyl or BOC.

In the process disclosed in WO 98/07694 for preparing compounds of formula I drug substance is obtained by separating two diastereoisomers of a late stage intermediate. This involves losing more than half of the material. Starting the present process with an optically active compound avoids this problem thus affording a significant improvement in yield and less waste.

In process step 2 the compound of formula VI where $R^1$, $R^2$ and $R^3$ are as hereinbefore defined and T is a protecting group is reacted with methanol, preferably in the absence of water, to give a compound of formula VII

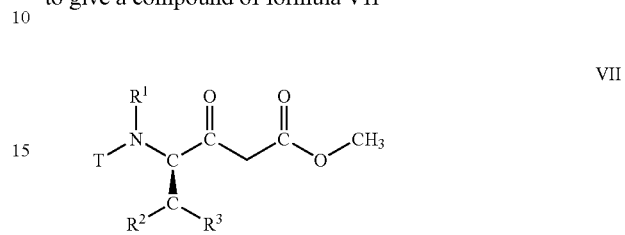

VII where $R^1$, $R^2$ and $R^3$ are as hereinbefore defined and T is a protecting group or analogously e.g. as hereinafter described in the Examples.

In process step 3 the compound of formula VII where $R^1$, $R^2$ and $R^3$ are as hereinbefore defined and T is a protecting group is reduced to give the corresponding (R)-hydroxy compound, i.e. a compound of formula VIII

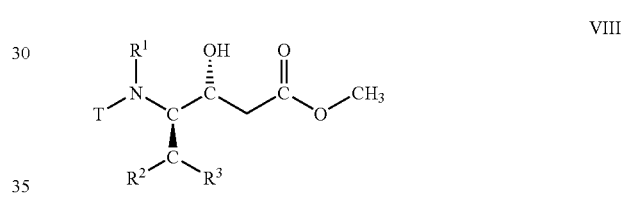

VIII where $R^1$, $R^2$ and $R^3$ are as hereinbefore defined and T is a protecting group. The reaction is carried out using known procedures for reducing ketones or analogously e.g. as hereinafter described in the Examples. The reaction is conveniently carried out in a mixture of organic solvents, for example tert-butyl methyl ether and methanol, and water. The reducing agent is suitably sodium borohydride. The reaction may be carried out at room temperature, but suitably from 15° C. to 25° C.

The (R)-hydroxy compound obtained has the right configuration for the later formation of the trans double bond.

In process step 4 the compound of formula VIII where $R^1$, $R^2$ and $R^3$ are as hereinbefore defined and T is a protecting group is hydrolysed to the give the corresponding carboxylic acid i.e. a compound of formula IX

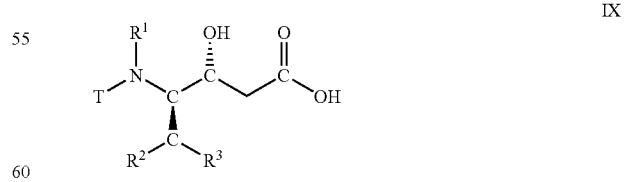

IX where $R^1$, $R^2$ and $R^3$ are as hereinbefore defined and T is a protecting group. The reaction is carried out using known procedures for hydrolysing esters to form carboxylic acids or analogously e.g. as hereinafter described in the Examples. The reaction is conveniently carried out in a mixture of a water soluble organic solvent, for example tert-butyl methyl ether and methanol, and water. The hydrolysing agent is suitably a strong base such as lithium hydroxide monohydrate. The reaction may be carried out at room temperature, but preferably from 15° C. to 25° C.

In process step 5 the compound of formula IX where $R^1$, $R^2$ and $R^3$ are as hereinbefore defined and T is a protecting group is reacted with a compound of formula X

where $R^5$ is $C_3$-$C_8$-cycloalkyl, D-azacycloheptan-2-on-3-yl or L-azacycloheptan-2-on-3-yl to form a compound of formula II

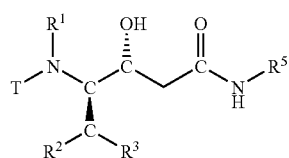

where $R^1$, $R^2$ and $R^3$ are as hereinbefore defined and T is a protecting group and $R^5$ is $C_3$-$C_8$-cycloalkyl, D-azacycloheptan-2-on-3-yl or L-azacycloheptan-2-on-3-yl.

The reaction is carried out using known procedures for reacting carboxylic acids with amines to form amide derivatives or analogously e.g. as hereinafter described in the Examples. The reaction is conveniently carried out in an organic solvent, for example N—N-dimethyl-formamide. The reaction is suitably carried out at room temperature, but preferably from 15° C. to 25° C.

In process step 6 the compound of formula II is purified, i.e. undesired isomers are removed. Surprisingly, this is achieved simply by stirring in an organic solvent, for example t-butyl methyl ether, at room temperature to 60° C., suitably 45° C. to 55° C., but especially suitably about 50° C., to give a product of high purity.

In process step 7 the compound of formula II where $R^1$, $R^2$, $R^3$ and $R^5$ are as hereinbefore defined and T is a protecting group is reacted with a base to form a compound of formula III

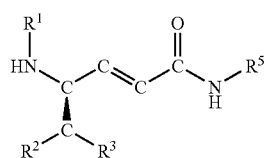

where $R^1$, $R^2$, $R^3$ and $R^5$ are as hereinbefore defined. Normally, in beta-hydroxy esters or amides, the hydroxyl group first has to be transformed into a leaving group prior to base-induced elimination under formation of the trans double bond. However, surprisingly, in process 7 the trans double bond is introduced in a one-step base-induced simultaneous removal of both, the (R)-hydroxy and the BOC moiety. Furthermore, the corresponding isomer compound having the hydroxyl group in the (S) configuration, does not undergo this reaction. The reaction is conveniently carried out in an organic solvent, for example tetrahydrofuran.

The reaction temperature may be, for example, from –10° C. to 10° C., suitably from –5° C. to 5° C., but especially suitably from –2° C. to 2° C. The reaction conditions given are optimised to keep the formation of by-products on a low level: with bases stronger than for example sodium ethoxide in ethanol, more cis bond formation, shifting of the double bond to form the ene-amine and epimerisation in the caprolactam moiety are observed. With weaker bases, long reaction times and only partial conversion are achieved.

In process step 8 the compound of formula III where $R^1$, $R^2$, $R^3$ and $R^5$ are as hereinbefore defined is reacted with a compound of formula IV

where R is phenyl that is unsubstituted or is substituted by 1, 2 or 3 substituents selected from the group consisting of halogen, $C_1$-$C_7$-alkyl, trifluoromethyl, hydroxy and $C_1$-$C_7$-alkoxy, and X is halo, suitably chloro, in the presence of a base to form a compound of formula I where R, $R^1$, $R^2$, $R^3$ and $R^5$ are as hereinbefore defined or a salt thereof.

The reaction is carried out using known procedures for reacting amines with acyl halides to form amide derivatives or analogously e.g. as hereinafter described in the Examples. The reaction is conveniently carried out in an organic solvent, for example tert-butyl methyl ether, and the base is for example triethylamine. The reaction temperature may be, for example, from –10° C. to 20° C., suitably from –5° C. to 15° C., but especially suitably from 0° C. to 5° C.

In process step 9, an optional step, the compound of formula I where R, $R^1$, $R^2$, $R^3$ and $R^5$ are as hereinbefore defined is crystallised in a suitable solvent to give the free compound, solvate or hydrate.

The compounds of formula I can be obtained in the form of the free compound, a hydrate or solvate thereof containing a solvent used for crystallization. For example when the compound of formula I is the compound of formula A it is crystallised from methanol and water to yield a stable drug substance hemihydrate.

The invention is illustrated by the following Example.

EXAMPLE

Preparation of N-[(E)-(R)-1-(3,4-Dichloro-benzyl)-3-((R)-2-oxo-azepan-3-ylcarbamoyl)-allyl]-N-methyl-3,5-bis-trifluoromethyl-benzamide Hemihydrate N-[(E)-(R)-1-(3,4-Dichloro-benzyl)-3-((R)-2-oxo-azepan-3-ylcarbamoyl)-allyl]-N-methyl-3,5-bis-trifluoromethyl-benzamide hemihydrate is prepared by the following process. All reactions are executed under a nitrogen atmosphere.

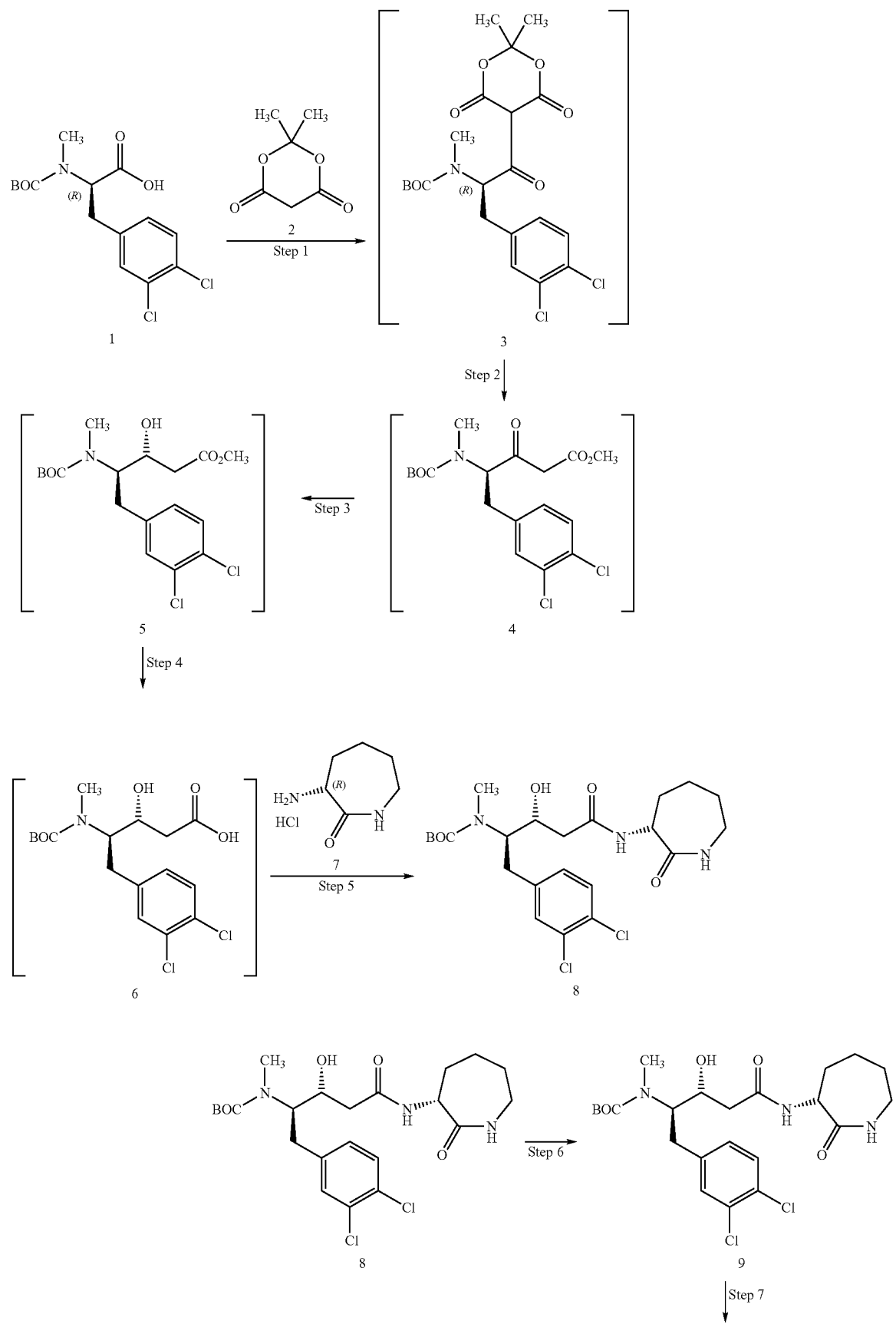

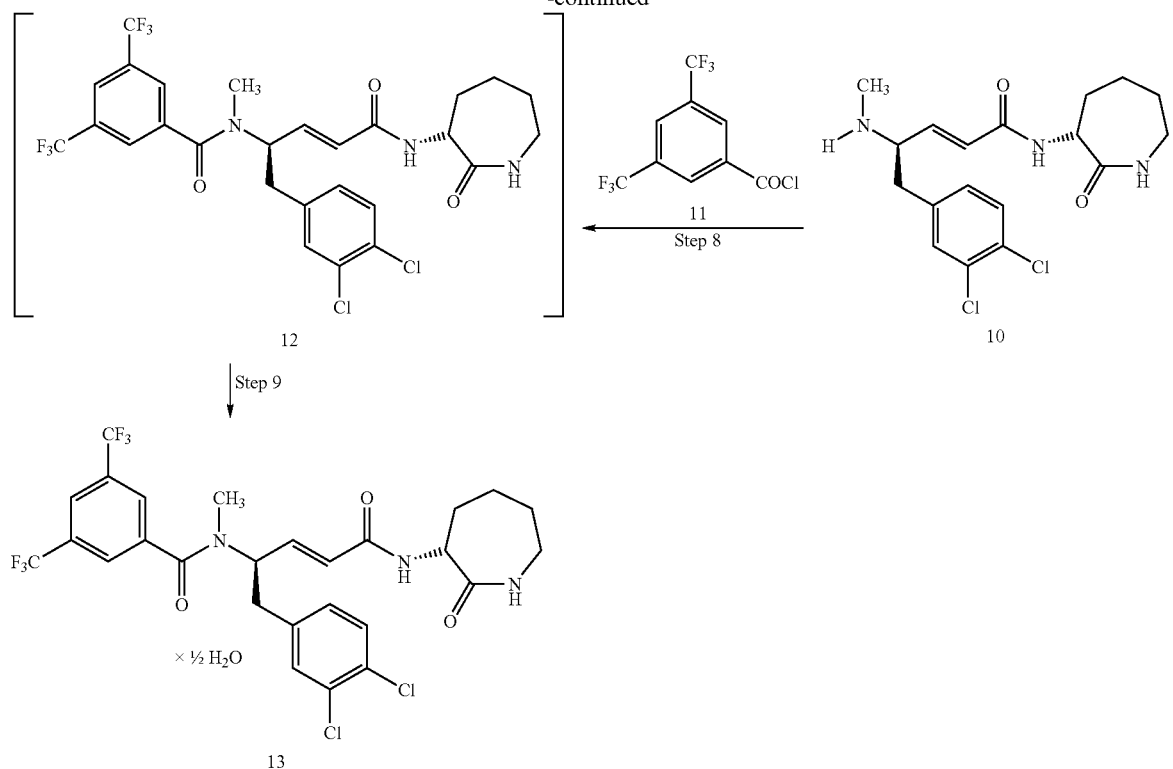

Steps 1+2: (R)-4-(tert-Butoxycarbonyl-methyl-amino)-5-(3,4-dichloro-phenyl)-3-oxo-pentanoic Acid Methyl Ester (4)

A solution of 1,3-dicyclohexylcarbodiimide (2.9011 g, 13.9 mmol) in toluene (3 ml) is added to a stirred mixture of (R)-2-(tert-butoxycarbonyl-methyl-amino)-3-(3,4-dichloro-phenyl)-propionic acid (1, 4.179 g, 12 mmol), 2,2-dimethyl-[1,3]dioxane-4,6-dione (2, 1.7815 g, 12.36 mmol) and dimethyl-pyridin-4-yl-amine (2.0943 g, 16.8 mmol) in toluene (32 ml) at 29-31° C. over a period of approx. 1 hour. Toluene (1 ml) is used for rinsing. Stirring at 29-31° C. is continued for approx. 3 hours. After cooling to ca. 0° C., a 25% w/w solution of potassium hydrogen sulfate (approx. 9 ml) is added to the suspension at −2° C./2° C., until pH 2-3 is reached. Stirring is stopped and the layers are allowed to separate. The mixture is slowly stirred and filtrated cold (0-5° C.) and the filter cake is rinsed with toluene (12 ml, 0-5° C.). The layers of the filtrate are allowed to separate at approx. 0-5° C. The lower, aqueous layer is separated. The upper, organic layer, containing the intermediate [(R)-1-(3,4-dichloro-benzyl)-2-(2,2-dimethyl-4,6-dioxo-[1,3]dioxan-5-yl)-2-oxo-ethyl]-methyl-carbamic acid tert-butyl ester (3) is passed through a filter charged with anhydrous sodium sulfate (5 g) at 0-5° C. and the filtrate is added to a reactor, containing methanol (18 ml, 20-25° C.). The filter cake is rinsed with toluene (5 ml) and the filtrate is also added to the reactor. The resulting solution is heated (mantle temperature ca. 68° C.) and stirred at approx. 63° C. for approx. 4 hours, then concentrated at a mantle temperature of approx. 50° C. under reduced pressure to obtain an oily residue, which is dissolved in tert-butyl methyl ether (24 ml) at normal pressure and a mantle temperature of ca. 50° C., then concentrated again under reduced pressure to obtain (R)-4-(tert-butoxycarbonyl-methyl-amino)-5-(3,4-dichloro-phenyl)-1-oxo-pentanoic acid methyl ester (4) as an oily residue. The residue is dissolved again in tert butyl methyl ether (24 ml) at normal pressure and a mantle temperature of 50° C., then cooled to 18-22° C. and used as such in the next step.

Step 3: (3R,4R)-4-(tert-Butoxycarbonyl-methyl-amino)-5-(3,4-dichloro-phenyl)-3-hydroxy-pentanoic Acid Methyl Ester (5)

Sodium borohydride (0.227 g, 6 mmol) is added to the stirred solution of (R)-4-(tert-butoxy-carbonyl-methyl-amino)-5-(3,4-dichloro-phenyl)-3-oxo-pentanoic acid methyl ester (4) in tert-butyl methyl ether at 18-22° C. Water (3 ml) is added over a period of approx. 20 minutes at 18-22° C., then stirring is continued for approx. 15 minutes. Methanol (3 ml) is added over a period of approx. 30 minutes at 18-22° C., then stirring is continued for approx. 30 minutes to give a solution of (3R,4R)-4-(tert-butoxycarbonyl-methyl-amino)-5-(3,4-dichloro-phenyl)-3-hydroxy-pentanoic acid methyl ester (5), which is used as such in the next step.

Step 4: (3R,4R)-4-(tert-Butoxycarbonyl-methyl-amino)-5-(3,4-dichloro-phenyl)-3-hydroxy-pentanoic Acid (6)

Water (3 ml) is added to the stirred reaction mixture containing (3R,4R)-4-(tert-butoxy-carbonyl-methyl-amino)-5-(3,4-dichloro-phenyl)-3-hydroxy-pentanoic acid methyl ester (5) at 18-22° C., then lithium hydroxide monohydrate (0.755 g, 18 mmol) is added. Stirring at 18-22° C. is continued for approx. 2 hours. Hydrochloric acid (approx. 12.6 ml of 2N, 25.2 mmol)) is added over a period of approx. 30 minutes, until pH 1.7-2.2 is obtained. Toluene (12 ml) is added to the stirred mixture and stirring at 18-22° C. is continued for approx. 10 minutes. Stirring is stopped and the layers are allowed to separate. The lower, aqueous layer is separated and the upper, organic layer is extracted with water (12 ml). Stirring is stopped and the lower, aqueous layer is separated. The organic layer is filtrated over a filter charged with anhydrous sodium sulfate (3 g) in order to remove remains of water and 1,3-dicyclohexyl urea, the latter originating from step 1. The filter cake is rinsed with toluene (2 ml), then N,N-dimethylformamide (12 ml) is added to the filtrate. The resulting solution is concentrated by distilling toluene at a mantle temperature of approx. 50° C. under reduced pressure, until the volume of the residue is approx. 14 ml. This resulting solution, containing (3R,4R)-4-(tert-butoxycarbonyl-methyl-amino)-5-(3,4-dichloro-phenyl)-3-hydroxy-pentanoic acid (6) is used as such in the following step.

Step 5: [(1R,2R)-1-(3,4-Dichloro-benzyl)-2-hydroxy-3-((R)-2-oxo-azepan-3-ylcarbamoyl)-propyl]-methyl-carbamic Acid tert-butyl Ester (8)

Triethylamine (1.396 g=1.91 ml, 13.8 mmol) is added to a stirred mixture of (R)-3-amino-azepan-2-one hydrochloride (7) in N,N-dimethylformamide (12 ml) at 18-22° C., then stirring is continued for approx. 1 hour. 1-Hydroxybenzotriazole hydrate (2.113 g, 13.8 mmol) is added at 18-22° C. to the stirred mixture, followed by the solution of (3R,4R)-4-tert-butoxycarbonyl-methyl-amino)-5-(3,4-dichloro-phenyl)-3-hydroxy-pentanoic acid (6) in N,N-dimethyl-formamide. N,N-dimethylformamide (2 ml) is used for rinsing. The mixture is cooled to 0-5° C., then 1,3-dicyclohexylcarbodiimide (2.847 g, 13.8 mmol) is added, followed by N,N-dimethyl-formamide (1.5 ml), used for rinsing. Stirring at approx. 0-5° C. is continued for approx. 1 hour, then the mixture is warmed to approx. 18-22° C. and stirred at that temperature for approx. 20 hours. The precipitated solids are removed by filtration and the filter cake is rinsed with N,N-dimethylformamide (12 ml). The filtrate is concentrated at a mantle temperature of approx. 60° C. under reduced pressure, until a concentrate of approx. 19.5 g is obtained. The resulting suspension is cooled to approx. 20-25° C., then an aqueous solution of potassium hydrogencarbonate (1.92 g, 19.17 mmol) in water (32 ml) is added over a period of approx. 20 minutes under evolution of carbon dioxide to give a suspension. The precipitated solids are isolated by filtration, rinsed with water (24 ml) and dried in vacuo at approx. 60° C. to constant weight to yield crude [(1R,2R)-1-(3,4-dichloro-benzyl)-2-hydroxy-3-((R)-2-oxo-azepan-3-ylcarbamoyl)-propyl]-methyl-carbamic acid tert-butyl ester (8) (6.019 g, 99.8% of theory based on (R)-2-(tert-butoxycarbonyl-methyl-amino)-3-(3,4-dichloro-phenyl-propionic acid (1).

Step 6: [(1R,2R)-1-(3,4-Dichloro-benzyl)-2-hydroxy-3-((R)-2-oxo-azepan-3-ylcarbamoyl)-propyl]-methyl-carbamic Acid tert-butyl Ester (9)

[(1R,2R)-1-(3,4-Dichloro-benzyl)-2-hydroxy-3-((R)-2-oxo-azepan-3-ylcarbamoyl)-propyl]-methyl-carbamic acid tert-butyl ester (8) (6.019 g) is added to stirred tert-butyl methyl ether (35 ml) at approx. 20-25° C. The mixture is heated to approx. 50-52° C. and stirred at that temp. for about 1 hour. The suspension is cooled to approx. 0-5° C. and stirred at that temperature for approx. 1 hour. The precipitated solids are isolated by filtration, rinsed with tert-butyl methyl ether (24 ml) and dried in vacuo at approx. 70° C. to constant weight to yield [(1R,2R)-1-(3,4-dichloro-benzyl)-2-hydroxy-3-((R)-2-oxo-azepan-3-ylcarbamoyl)-propyl]-methyl-carbamic acid tert-butyl ester (9) (4.2625 g, 70.7% of theory based on (R)-2-(tert-butoxy-carbonyl-methyl-amino)-3-(3,4-dichloro-phenyl-propionic acid (1). Purity: 98.5% area (hplc). The product is further purified by crystallization from dichloromethane/tert-butyl methyl ether: m.p. 186.8-187.4° C., MS-ES$^+$: (MNa)$^+$=524 ($^{35}Cl_2$), $[\alpha]_D^{20}$=+17.24° (ethanol 94%).

Step 7: (E)-(R)-5-(3,4-Dichloro-phenyl)-4-methylamino-pent-2-enoic Acid ((R)-2-oxo-azepan-3-yl)-amide (10)

A stirred mixture of [(1R,2R)-1-(3,4-dichloro-benzyl)-2-hydroxy-3-((R)-2-oxo-azepan-3-yl-carbamoyl)-propyl]-methyl-carbamic acid tert-butyl ester (9) (1.005 g, 2.0 mmol) and tetra-hydrofuran (12 ml) is cooled to −2° C./2° C., then a 21% w solution of sodium ethoxide in ethanol (1.5 ml, 4.0 mmol) is added at −2° C./2° C. over a period of approx. 20 minutes. The resulting solution is stirred at approx. 0° C. for about 4.5 hours, then a 5% w aqueous solution of potassium hydrogencarbonate (0.253 g, 2.53 mmol in 4.81 g water) is added at approx. 0° C. over a period of approx. 10 minutes. The temperature is raised to approx. 20° C., then toluene (17 ml) is added. After stirring the mixture for approx. 16 hours at ca. 20° C., stirring is stopped and the layers are allowed to separate. The lower, aqueous layer is separated and the organic layer is extracted with water (3.5 ml). The organic layer is concentrated at a mantle temp. of 60° C. under reduced pressure, until approx. 10 g of residue are obtained, causing the product to crystallise. After stirring at 60° C. for approx. 10 minutes, distillation is continued, until a residue of about 5 g is obtained. Water (0.36 ml) is added and stirring at 60° C. is continued for approx. 30 minutes. The mixture is cooled to about 0° C. over a period of ca. 30 minutes, then stirring at that temperature is continued for approx. 2 hours. The precipitated solids are isolated by filtration and the filter cake is rinsed with toluene (3 ml). After drying at approx. 60° C. in vacuo to constant weight, (E)-(R)-5-(3,4-dichloro-phenyl)-4-methylamino-pent-2-enoic acid ((R)-2-oxo-azepan-3-yl)-amide (10) (0.580 g, 75.5% of theory based on (9) is obtained: m.p. 153-158° C., MS-ES$^+$: (MH)$^+$=384 ($^{35}Cl_2$), $[\alpha]_D^{20}$=80.4° (ethanol).

Step 8: N-[(E)-(R)-1-(3,4-Dichloro-benzyl)-3-((R)-2-oxo-azepan-3-ylcarbamoyl)-allyl]-N-methyl-3,5-bis-trifluoromethyl-benzamide (12)

A stirred mixture of E)-(R)-5-(3,4-dichloro-phenyl)-4-methylamino-pent-2-enoic acid ((R)-2-oxo-azepan-3-yl)-amide (10) (1.1529 g, 3 mmol) in tert-butyl methyl ether (10 ml) is cooled to approx. 0° C. 3,5-bis-trifluoromethyl-benzoyl chloride (0.87 g=0.57 ml, 3.15 mmol) is added at 0-5° C. over a period of approx. 15 minutes followed by triethylamine (0.319 g=0.44 ml, 3.15 mmol), which is added at approx. 0-5° C. over a period of approx. 30 minutes. Stirring at 0-5° C. is continued for approx. 10 minutes, then the mixture is warmed to 20-25° C. over a period of approx. 30 minutes. The precipitated solids are removed by filtration and the filter cake is rinsed with tert-butyl methyl ether (5 ml). The filtrate is stirred and methanol (3 ml) is added. The solution is concentrated by distilling at a mantle temperature of approx. 50° C. under reduced pressure, until a residue of approx. 10.5 ml is obtained. Methanol (8.5 ml) is added and the solution is concentrated again by distilling at a mantle temperature of approx. 50° C. under reduced pressure, until a residue of approx. 10.5 ml is obtained. Again, methanol (8.5 ml) is added and the solution is concentrated by distilling at a mantle temperature of approx. 50° C. under reduced pressure, until a residue of approx. 10.5 ml is obtained. The solution containing N-[(E)-(R)-1-(3,4-dichloro-benzyl)-3-((R)-2-oxo-azepan-3-ylcarbamoyl)-allyl]-N-methyl-3,5-bis-trifluoromethyl-benzamide (12) is cooled to 18-22° C. and used as such in the next step.

Step 9: N-[(E)-(R)-1-(3,4-Dichloro-benzyl)-3-((R)-2-oxo-azepan-3-ylcarbamoyl)-allyl]-N-methyl-3,5-bis-trifluoromethyl-benzamide Hemihydrate (13)

Water (2.6 ml) is added to the stirred solution (10.5 ml) of N-[(E)-(R)-1-(3,4-dichloro-benzyl)-3-((R)-2-oxo-azepan-3-ylcarbamoyl)-allyl]-N-methyl-3,5-bis-trifluoromethyl-benzamide (12) in methanol at approx. 18-22° C., whereupon crystallisation begins. After stirring for approx. 10 minutes, water (1 ml) is added at 18-22° C. over a period of approx. 20 minutes. Stirring at 18-22° C. is continued for 2 hours. The precipitated solids are isolated by filtration and the filter cake is rinsed with a mixture of methanol and water (2 ml+1 ml), followed by water (3 ml). The solids are dried at 30° C. in vacuo to constant weight to yield N-[(E)-(R)-1-(3,4-dichloro-benzyl)-3-((R)-2-oxo-azepan-3-ylcarbamoyl)-allyl]-N-methyl-3,5-bis-trifluoromethyl-benzamide hemihydrate (13) [1.6241b=85.5% of theory based on (E)-(R)-5-(3,4-dichloro-phenyl)-4-methylamino-pent-2-enoic acid ((R)-2-oxo-azepan-3-yl)-amide (10)], m.p. 127-131° C., sintering >123° C., MS-ES$^+$: (MH)$^+$=624 ($^{35}$Cl$_2$), [α]$_D^{20}$=+40.6° (methanol).

The invention claimed is:

1. A process for preparing compounds of formula I

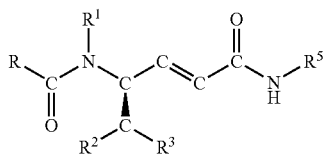

I or a solvate or hydrate thereof, where

R is phenyl that is unsubstituted or is substituted by 1, 2 or 3 substituents selected from the group consisting of halogen, $C_1$-$C_7$-alkyl, trifluoromethyl, hydroxy and $C_1$-$C_7$-alkoxy;

$R^1$ is hydrogen or $C_1$-$C_7$-alkyl;

$R^2$ is hydrogen, $C_1$-$C_7$-alkyl or phenyl that is unsubstituted or is substituted by 1, 2 or 3 substituents selected from the group consisting of halogen, $C_1$-$C_7$-alkyl, trifluoromethyl, hydroxy and $C_1$-$C_7$-alkoxy;

$R^3$ is phenyl that is unsubstituted or is substituted by 1, 2 or 3 substituents selected from the group consisting of halogen, $C_1$-$C_7$-alkyl, trifluoromethyl, hydroxy and $C_1$-$C_7$-alkoxy, or $R^3$ is naphthyl, 1H-indol-3-yl or 1-$C_1$-$C_7$-alkyl-indol-3-yl; and $R^5$ is $C_3$-$C_8$-cycloalkyl, D-azacycloheptan-2-on-3-yl or L-azacycloheptan-2-on-3-yl, the process comprising the steps of:

(a) reacting a compound of formula II

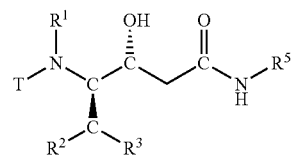

II where $R^1$, $R^2$, $R^3$ and $R^5$ are as defined in this claim above and T is a BOC protecting group, with a base to form a compound of formula III

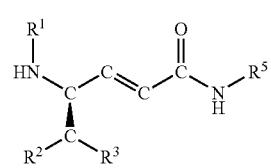

III where $R^1$, $R^2$, $R^3$ and $R^5$ are defined in this claim above; and (b) reacting a compound of formula III where $R^1$, $R^2$, $R^3$ and $R^5$ are as defined in this claim above with a compound of formula IV

IV where R is phenyl that is unsubstituted or is substituted by 1, 2 or 3 substituents selected from the group consisting of halogen, $C_1$-$C_7$-alkyl, trifluoromethyl, hydroxy and $C_1$-$C_7$-alkoxy, and X is halo, in the presence of a base to form a compound of formula I, and (c) optionally, forming a desired solvate or hydrate thereof.

2. A process according to claim 1 wherein the base used in step (a) is sodium ethoxide.

3. A process according to claim 1 wherein the compound of formula II where $R^1$, $R^2$, $R^3$, $R^5$ and T are as defined in claim 1 is prepared by the steps of:

(i) reacting a compound of formula V

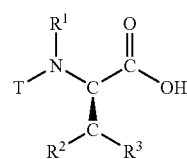

V where $R^1$, $R^2$ and $R^3$ are as defined in claim 1 and T is a BOC protecting group with 2,2-dimethyl-[1,3]dioxane-4,6-dione in the presence of a base to form a compound of formula VI

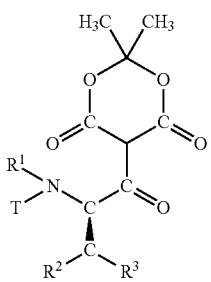

VI where R$^1$, R$^2$ and R$^3$ are as defined in claim 1 and T is a BOC protecting group;

(ii) reacting the compound of formula VI where R$^1$, R$^2$ and R$^3$ are as defined in claim 1 and T is a BOC protecting group with methanol to give a compound of formula VII

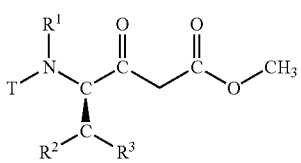

VII where R$^1$, R$^2$ and R$^3$ are as defined in claim 1 and T is a BOC protecting group;

(iii) reducing the compound of formula VII where R$^1$, R$^2$ and R$^3$ are as defined in claim 1 and T is a BOC protecting group to form a compound of formula VIII

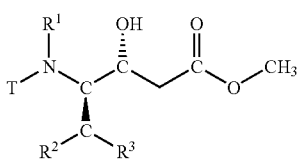

VIII where R$^1$, R$^2$ and R$^3$ are as defined in claim 1 and T is a BOC protecting group;

(iv) hydrolysing the compound of formula VIII where R$^1$, R$^2$ and R$^3$ are as defined in claim 1 and T is a BOC protecting group to give the corresponding carboxylic acid of formula IX

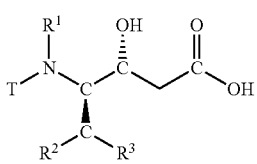

IX where R$^1$, R$^2$ and R$^3$ are as defined in claim 1 and T is a BOC protecting group; and (v) reacting the compound of formula IX where R$^1$, R$^2$ and R$^3$ are as defined in claim 1 and T is a BOC protecting group with a compound of formula X

H$_2$N—R$^5$     X where R$^5$ is C$_3$-C$_8$-cycloalkyl, D-azacycloheptan-2-on-3-yl or L-azacycloheptan-2-on-3-yl.

4. A process according to claim 1 wherein the compound of formula I is (4R)-4-[N'-methyl-N'-(3,5-bistrifluoromethyl-benzoyl)-amino]-4-(3,4-dichlorobenzyl)-but-2-enoic acid N-[(R)-epsilon-caprolactam-3-yl]-amide hemihydrate.

5. A process for preparing compounds of formula I as claimed in claim 1, the process comprising the steps of:

(i) reacting a compound of formula V

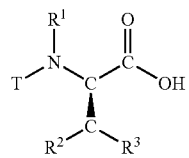

V where R$^1$, R$^2$ and R$^3$ are as defined in claim 1 and T is a BOC protecting group with 2,2-dimethyl-[1,3]dioxane-4,6-dione in the presence of a base to form a compound of formula VI

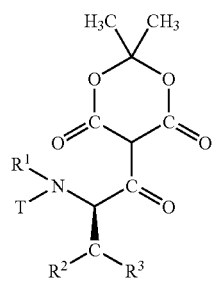

VI where R$^1$, R$^2$ and R$^3$ are as defined in claim 1 and T is a BOC protecting group;

(ii) reacting the compound of formula VI where R$^1$, R$^2$ and R$^3$ are as defined in claim 1 and T is a BOC protecting group with methanol to give a compound of formula VII

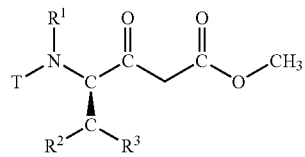

VII where R$^1$, R$^2$ and R$^3$ are as defined in claim 1 and T is a BOC protecting group;

(iii) reducing the compound of formula VII where R$^1$, R$^2$ and R$^3$ are as defined in claim 1 and T is a BOC protecting group to form a compound of formula VIII

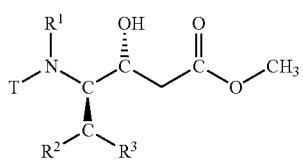

VIII where $R^1$, $R^2$ and $R^3$ are as defined in claim 1 and T is a BOC protecting group;

(iv) hydrolysing the compound of formula VIII where $R^1$, $R^2$ and $R^3$ are as defined in claim 1 and T is a BOC protecting group to give the corresponding carboxylic acid of formula IX

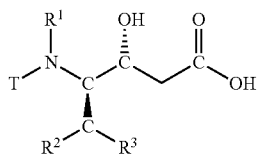

IX where $R^1$, $R^2$ and $R^3$ are as defined in claim 1 and T is a BOC protecting group;

(v) reacting the compound of formula IX where $R^1$, $R^2$ and $R^3$ are as defined in claim 1 and T is a BOC protecting group with a compound of formula X $H_2N$—$R^5$    X where $R^5$ is $C_3$-$C_8$-cycloalkyl, D-azacycloheptan-2-on-3-yl or L-azacycloheptan-2-on-3-yl to form a compound of formula II

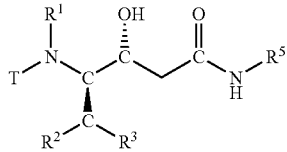

II where $R^1$, $R^2$ and $R^3$ are as defined in claim 1 and T is a BOC protecting group and $R^5$ is $C_3$-$C_8$-cycloalkyl, D-azacycloheptan-2-on-3-yl or L-azacycloheptan-2-on-3-yl;

(vi) optionally, purifying the compound of formula II where $R^1$, $R^2$, $R^3$ and $R^5$ are as defined in claim 1 and T is a BOC protecting group;

(vii) reacting the compound of formula II where $R^1$, $R^2$, $R^3$ and $R^5$ are as defined in claim 1 and T is a BOC protecting group, with a base to form a compound of formula III

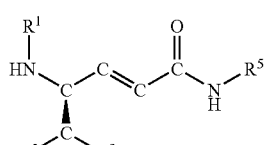

III where $R^1$, $R^2$, $R^3$ and $R^5$ are as defined in claim 1;

(viii) reacting the compound of formula III where $R^1$, $R^2$, $R^3$ and $R^5$ are as defined in claim 1 is reacted with a compound of formula IV

IV where R is phenyl that is unsubstituted or is substituted by 1, 2 or 3 substituents selected from the group consisting of halogen, $C_1$-$C_7$-alkyl, trifluoromethyl, hydroxy and $C_1$-$C_7$-alkoxy, and X is halo, in the presence of a base to form a compound of formula I where R, $R^1$, $R^2$, $R^3$ and $R^5$ are as defined in claim 1; and (ix) optionally, forming a desired solvate or hydrate.

* * * * *